United States Patent
Beerman et al.

(10) Patent No.: US 9,687,382 B2
(45) Date of Patent: Jun. 27, 2017

(54) SUPPORT DEVICE FOR MALE GENITALIA

(71) Applicants: Julia Beerman, Fort Wayne, IN (US); Kara Lowenstein, Fort Wayne, IN (US); Solomon L. Lowenstein, Jr., Bloomington, IN (US)

(72) Inventors: Julia Beerman, Fort Wayne, IN (US); Kara Lowenstein, Fort Wayne, IN (US); Solomon L. Lowenstein, Jr., Bloomington, IN (US)

( * ) Notice: Subject to any disclaimer, the term of this patent is extended or adjusted under 35 U.S.C. 154(b) by 0 days.

(21) Appl. No.: 14/567,485

(22) Filed: Dec. 11, 2014

(65) Prior Publication Data
US 2016/0166423 A1    Jun. 16, 2016

(51) Int. Cl.
*A61F 13/00*    (2006.01)
*A61F 5/40*    (2006.01)

(52) U.S. Cl.
CPC ................................ *A61F 5/40* (2013.01)

(58) Field of Classification Search
CPC ......... A61F 5/40; A63B 71/1216; A41B 9/02; A43B 71/08
USPC ......... 602/67–70, 72, 73; D2/711, 713, 714, D2/701
See application file for complete search history.

(56) References Cited

U.S. PATENT DOCUMENTS

| | | | | |
|---|---|---|---|---|
| 757,153 A * | 4/1904 | Tainsh | ...................... | A61F 5/40 602/73 |
| 909,948 A * | 1/1909 | Schmertz | .................. | A61F 5/40 602/71 |
| 1,074,147 A * | 9/1913 | Whitlock | .................. | A61F 5/40 602/70 |
| 1,164,950 A * | 12/1915 | Martin | ...................... | A61F 5/40 602/73 |
| 1,320,737 A * | 11/1919 | Chilsholm | ................ | A61F 5/40 602/73 |
| 1,350,863 A * | 8/1920 | Fowler | ...................... | A61F 5/40 602/70 |
| 1,477,187 A * | 12/1923 | Rayne | ...................... | A61F 5/40 602/71 |
| 1,610,531 A * | 12/1926 | Morrison | .................. | A61F 5/40 602/73 |
| 2,576,024 A | 11/1951 | Laser | | |
| 2,746,453 A * | 5/1956 | Johnson | .................... | A61F 5/40 602/70 |
| 2,888,014 A * | 5/1959 | Dougherty | ................ | A61F 5/40 602/70 |

(Continued)

FOREIGN PATENT DOCUMENTS

| | | |
|---|---|---|
| CN | 201275169 | 7/2009 |
| CN | 201286787 | 8/2009 |

(Continued)

OTHER PUBLICATIONS

Cazenave C et al., Scrotal Cup for Testicular Ultrasound, Journal of Clinical Ultrasound 15(5): pp. 357-359, 1987.*

(Continued)

*Primary Examiner* — Kim M Lewis
(74) *Attorney, Agent, or Firm* — John D Ritchison; Ritchison Law Offices, PC

(57) ABSTRACT

Provided is a support device for supporting male genitalia, particularly the scrotum, when a male is in a seated position, including a support member and two or more attachment members for attachment to or hanging from a user's legs.

12 Claims, 2 Drawing Sheets

(56) References Cited

U.S. PATENT DOCUMENTS

| | | | | |
|---|---|---|---|---|
| RE24,906 E | * | 12/1960 | Ulrich | A61L 15/585 |
| | | | | 427/208 |
| 3,153,412 A | * | 10/1964 | Laubsch | A61F 5/40 |
| | | | | 128/845 |
| 3,295,520 A | | 1/1967 | Keller | |
| 3,314,422 A | * | 4/1967 | Phillips | A41B 9/02 |
| | | | | 128/846 |
| 3,990,119 A | | 11/1976 | Barrett | |
| 4,378,010 A | * | 3/1983 | McDonald | A61B 19/00 |
| | | | | 128/DIG. 26 |
| 4,487,202 A | * | 12/1984 | Sachse | A61F 5/40 |
| | | | | 600/38 |
| 4,622,962 A | * | 11/1986 | Kauffman | A61F 5/40 |
| | | | | 602/70 |
| 5,036,839 A | | 8/1991 | Weiss | |
| 5,094,234 A | * | 3/1992 | Searcy | A61F 5/40 |
| | | | | 602/68 |
| 5,547,466 A | | 8/1996 | McRoberts et al. | |
| 5,807,299 A | * | 9/1998 | McRoberts | A61F 5/40 |
| | | | | 602/67 |
| 6,245,036 B1 | | 6/2001 | McRoberts et al. | |
| 7,100,213 B2 | * | 9/2006 | Krautbauer | A41B 9/023 |
| | | | | 2/400 |
| 8,622,948 B2 | | 1/2014 | Gedeon | |
| 2004/0199046 A1 | * | 10/2004 | Astin | A61F 5/40 |
| | | | | 600/38 |
| 2004/0199091 A1 | | 10/2004 | Vogelsang-Switzer | |
| 2006/0211974 A1 | * | 9/2006 | Bland | A61F 5/40 |
| | | | | 602/67 |
| 2006/0211975 A1 | * | 9/2006 | Mular | A61F 5/40 |
| | | | | 602/70 |
| 2007/0044209 A1 | * | 3/2007 | Maurer | A61F 5/40 |
| | | | | 2/403 |
| 2008/0099028 A1 | * | 5/2008 | Mular | A61F 5/40 |
| | | | | 128/845 |
| 2013/0291879 A1 | * | 11/2013 | Matsuda | A61F 2/0009 |
| | | | | 128/885 |

FOREIGN PATENT DOCUMENTS

| | | | |
|---|---|---|---|
| CN | 201782854 | | 4/2011 |
| CN | 201840558 | | 5/2011 |
| CN | 202920422 | | 5/2013 |
| CN | 203074961 | | 7/2013 |
| CN | 203074962 | | 7/2013 |
| CN | 203074963 | | 7/2013 |
| CN | 203169382 | | 9/2013 |
| GB | 190012839 A | * | 0/1901 |
| JP | 5181381 | | 4/2013 |
| SU | 1132938 A | * | 1/1985 |

OTHER PUBLICATIONS http://www.amazon.com/Suspensory-Jockstrap-Scrotal-Testicle-Support/dp/B0050HR23Q, Suspensory Jockstrap for Scrotal/Testicle Support by Flexmead, displayed as of Aug. 24, 2014 in the USA.
http://scientopia.org/blogs/scicurious/2010/06/18/friday-weird-science-a-tote-for-your-scrote-a-recepticle-for-your-testicle/, "Friday Weird Science" published on Jun. 18, 2010, p. 1 and image on p. 5.

* cited by examiner

SUPPORT DEVICE FOR MALE GENITALIA

BACKGROUND

It is a common problem for older males to suffer various inconveniences related to the positioning of the scrotum, and particularly the distance of hang of the scrotum and scrotal sack. When a man is engaged in many activities of daily life, the scrotum can be supported by undergarments such as briefs. In some activities, however, such as using a toilet, undergarment support is not available. In these instances, the increased hang distance of the scrotum experienced by many older men may cause a number of inconveniences, such as unwanted contact between the scrotum and the toilet water or other contents of the toilet.

Some men experiencing undue scrotal hang, particularly due to age, require general age- or condition-related medical treatment that may include assistance going to the bathroom and with hygiene, such as taking showers or baths. For example, some elderly men live in nursing homes, hospice facilities, or other assisted-living facilities in which care providers assist with tasks like going to the bathroom arid taking showers. For men experiencing undue distance of scrotal hang, the unwieldy nature of the hanging scrotum and the increased potential for unwanted contact between the scrotum and the contents of a toilet can make the task of as care provider more dangerous, particularly if the care provider is required to assist with scrotal cleaning after the man has used the toilet. This can also result in serious discomfort to the man whose scrotum is being cleaned.

In some circumstances, a man experiencing undue scrotal hang may, when using the toilet, suffer direct contact between his scrotum and toilet water and its contents, which may include urine, blood, or fecal matter. These undesirable, and often pathogenic, substances must then be cleaned from the scrotum either by the man or by a care provider.

The scrotum is a sensitive part of the male anatomy. The scrotum has thin skin, and contact with the scrotum can be painful. Any method of support for the scrotum must account for its weight, size, and, most of all, sensitivity to touch and to pain.

A number of health-related devices are known to the art to provide scrotal support in the context of health care, particularly when a man is either standing and active, or, alternatively, when he is laying down. When a man is standing or active, it is well known to the art to use a jock-strap type of support, where a sling configured to hold the scrotum is attached to a belt around the man's waist. A number of devices are also known to the art to support the scrotum of a recumbent man. For example, U.S. Pat. No. 6,308,710 presents support that functions as a sling to hold the scrotum up during medical analysis and treatment. U.S. Patent Publication No. 2008/0099028 discloses a sling for scrotal support when as male is recumbent, such as when a male patient is sedated or sleeping. U.S. Patent Pub. No. 2004/0199091, similarly, discloses a sling-configuration support device for supporting the scrotum of a recumbent man. U.S. Pat. No. 4,487,202 discloses a profiled block apparatus designed to hold the scrotum in place, again, similarly, when a male patient is recumbent.

There is a need for a device that supports a man's scrotum and prevents undue scrotal hang when the man is seated without other scrotal support, such as when using a toilet. Such a device should support the scrotum sufficiently to prevent it from contacting the toilet water or toilet contents such as urine blood, or feces, should be sufficiently comfortable to accommodate the sensitive scrotum, and, since the device is likely to encounter pathogenic substances like feces, should be disposable or easily cleanable. Still floater, there is a need for a method for supporting male genitalia that does not require the placement of briefs or a support device around the patient's waist.

SUMMARY OF INVENTION

A device for supporting a male scrotum when the male is in a seated position, and particularly when using the toilet, is provided. In a first embodiment, the support device is disposable and comprises a flexible support member and two or more attachment members to removably attach the support member to the user's thighs such that the support, member is suspended under the user's scrotum and prevents undue hang of the scrotum. In a second embodiment, the support device is easily cleanable and comprises a support member and two or more outwardly depending wings configured to rest upon the tops of the user's thighs such that the support member is suspended under the user's scrotum and prevents undue hang of the scrotum.

BRIEF DESCRIPTION OF THE DRAWINGS

So that the manner in which the features of the present invention can be better understood, certain drawings are shown. It is to be noted, however, that these illustrations depict only selected embodiments of the inventions and systems and are not to be considered limiting of scope, for the inventions may admit to other equally effective embodiments and applications.

DETAILED DESCRIPTION OF THE INVENTION

For purposes herein, "scrotum" refers to the common anatomical male feature of a pouch of skin containing one or more, and most commonly two, testicles. A man's scrotum is, for the purposes of this invention, considered to hang unduly or to suffer undue hang when any portion of his scrotum is at or substantially near the level of the water of a toilet at an point while he sits upon the toilet to use it. As will be appreciated by one skilled in the art, the proximity of a man's scrotum to the water level of a toilet depends upon a number of variables, such as the size and length of the scrotum, the type and configuration of the toilet, the overall size and shape of the man's legs and buttocks, and the thickness of the toilet seat. Accordingly, whether a man's scrotum is considered to hang unduly o to suffer undue hang for purposes of this invention is determined subjectively according to an individual determination by the man, his care provider, or another individual that the scrotum is touching, is likely to touch, or is too close to the undesired contents of as toilet, and is not determined as a function of any particular objective measure of scrotal size or length, or any particular distance from the water level of a toilet.

Figure 1:
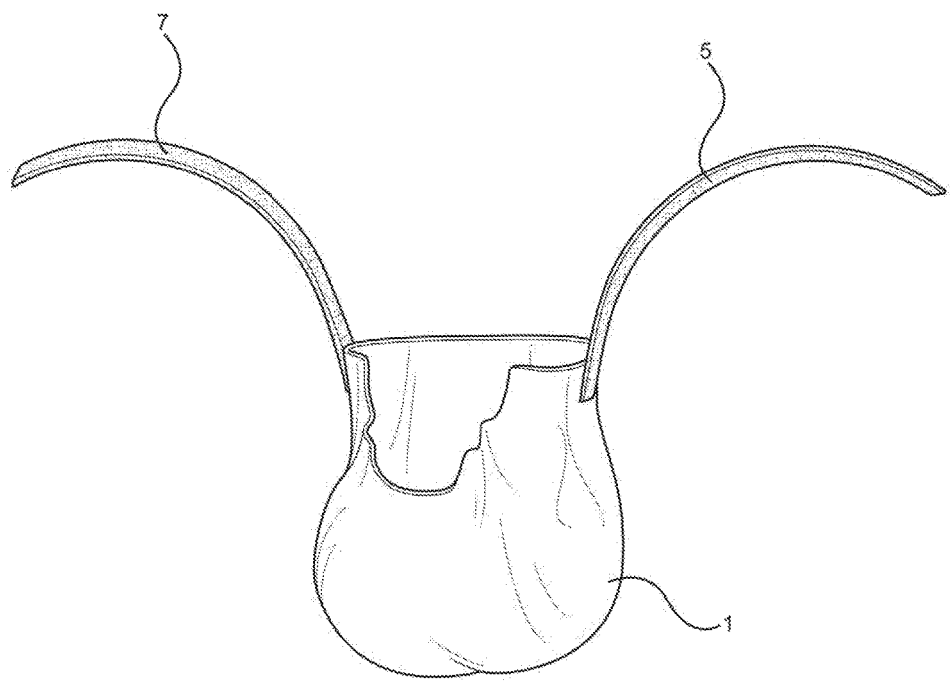
FIG. 1 shows a perspective view of a first embodiment of the present invention, in which the scrotal support member is flexible and disposable.

Referring now to FIG. 1, in one embodiment the present invention comprises a support member (1) detachably attached to two or more attachment members. A support member (1) according to one embodiment of the present invention comprises a surface that will prevent a man's scrotum from undue hang when the support member (1) is attached to two or more attachment members and said attachment members are attached to a user's thighs so that the support member (1) is positioned under and supports the user's scrotum. In these embodiments of the invention, the support member (1) is flexible and disposable. A support member (1) according to these embodiments of the invention may be made of a variety of flexible disposable materials, including thin textiles, woven cloths, non-woven cloths, and flexible polymers. In a preferred embodiment, the support member (1) is composed of thin, flexible, disposable plastic, such as cellophane.

A support member (1) in these embodiments of the invention is sized and shaped to accommodate a wide variety of sizes of scrota. In preferred embodiments, the support member (1) has a generally bag-like shape approximately complimentary to the overall shape of most male scrota and is four inches or less in overall depth, with a profiled cutout on its front side to allow the penis to hang outside of, and not be captive by or within, the support member (1). As will be appreciated by one skilled in the art, however, a variety of sizes and shapes are possible within the scope and spirit of this invention.

The support member (1) is in these embodiments detachably attached to two or more attachment members. In a preferred embodiment, the support member (1) is detachably attached to a first attachment member (5) on a first side of the support member (1), and detachably attached to a second attachment member (7) on a second side of the support member (1) opposite the first side of the support member (1). Preferably, the first side of the support member (1) is located to one side of the scrotum at a point approaching one of the user's legs, and the second side of the support member (1) is located to an opposite side of the scrotum approaching the other of the user's legs. In a preferred embodiment, the attachment members attach to the support member (1) by adhesive connection. Optionally, the attachment members may be mechanically attached to the support member (1) by a mechanical connection other than adhesive, or, still further optionally, may be integral to the support member (1).

In the depicted preferred embodiment, the support member (1) is a bag with a mouth wider than the user's scrotum and a profiled cut-out to allow escape of at least a portion of the user's penis, and the attachment members are detachably attached to the support member (1) at locations near the mouth of the bag and at opposite sides. As will be appreciated by one skilled in the art, a number of attachment locations and configurations of attachment member to support member (1) are possible within the scope and spirit of this invention.

Attachment members, including at least the first attachment member (5) and second attachment member (5), attach to the legs of a user, and preferably to the inner or upper thighs. In a preferred embodiment, a first attachment member (5) attaches to one leg of the user, and a second attachment member (7) attaches to the other leg of the user. Attachment members of these embodiments preferably attach to the legs of a user by removable adhesive connection to skin or clothing. In this way, the fit of the device can he customized by moving one or more attachment members to different locations on the user's legs. For example, the device can provide enhanced support and allow less scrotal hang if attachment members are attached higher on a user's leg, or further forward, or both. The device can provide enhanced comfort and allow greater hang if one or more attachment members are attached lower or further back on the user's legs. Asymmetries in the user's body, particularly in his scrotum, can be addressed by adjusting the attachment point of each attachment member individually for optimal fit that balances the user's preferences for comfort and amount of scrotal hang. As will be appreciated by one skilled in the art, similar customization of fit can be accomplished in some embodiments by altering the attachment point or one or more attachment members to the support member (1). A device within the scope and spirit of this invention may include three, four, or more attachment members.

Attachment members in these embodiments are flexible and disposable. Preferably, the first attachment member (5) and second attachment member (7) are comprised of an adhesive ribbon, such as disposable and easily removable adhesive tape, most preferably surgical tape. As will be appreciated by one skilled in the art, the attachment members may be composed of a wide variety of adhesive tapes or ribbons within the scope and spirit of this invention.

Figure 2:
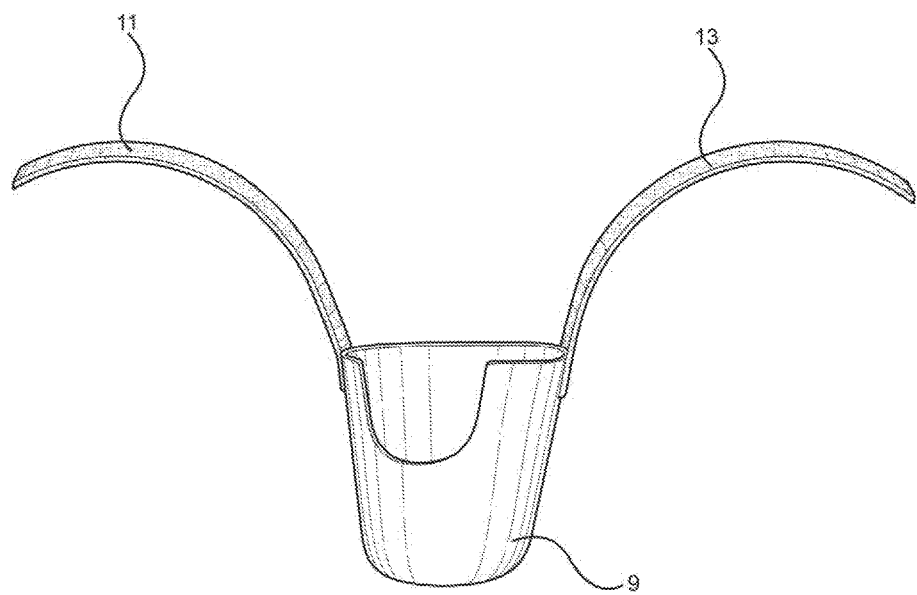
FIG. 2 shows a perspective view of a second embodiment of the present invention, which the scrotal support member comprises outwardly depending wings.

Referring now to FIG. 2, in an alternative preferred embodiment, the device is easily cleanable and non-disposable. In this embodiment, the device comprises a support member (9) and two or more outwardly depending wings configured to rest on top of a user's thighs so that the support member (9) supports the user's scrotum and prevents undue hang. For purposes of discussion of these embodiments, a substance is considered "cleanable" if pathogenic substances such as feces can be easily removed by wiping the substance clean with soap and water without substantial scrubbing. "Cleanable" substances are disclosed in more detail below, but, as will be appreciated by one skilled in the art, include commonly-used medical plastics and stainless steels, and preferably include dishwasher-safe materials.

A support member (9) in these embodiments of the invention is sized and shaped to accommodate a wide variety of sizes of scrota. The support member (9) is relatively rigid and is composed of a cleanable and substantially inflexible material, such as HDPE, PVC, polypropylene, Lexan, or other plastics. As will be appreciated by one skilled in the art, other cleanable materials, such as stainless steel or PEEK, may be used.

In preferred embodiments, the support member (9) has to generally cup-like shape approximately complimentary to the overall shape of most male scrota and is four inches or less in overall depth. Preferably, the support member (9) includes a profiled cut-out to allow at least a portion of the penis to escape and not be captured by the support member (9) when the device is in use. As will be appreciated by one skilled in the art, a variety of sizes and shapes of support member (9) are possible within the scope and spirit of this invention.

The support member (9) is in these embodiments attached to two or more wings. The wings are, preferably, made of a cleanable, rigid material similar to the support member (9), and most preferably are made of the same material. In a preferred embodiment, the support member (9) is integrally attached to a first wing (11) outwardly depending from a first side of the support member (9) to one side of the scrotum, in the direction of the user's leg on that first side, and is integrally attached to a second wing (13) outwardly depending from a second side of the support member (9) opposite the first side, in the direction of the user's other leg. In this alternative preferred embodiment, the first wing (11) and second wing (13) depend from the support member (9) both outwardly away from the scrotum and towards the user's legs and upwardly away from the scrotum and towards the tops of the user's thighs when seated, so that in use, each wing rests across one of the user's legs and the support member (9) is suspended between the wings in a location suitable to support the user's scrotum and prevent undue hang. Herein, the distance that a wing extends from the scrotum towards a user's leg when the user is seated will be referred to as "outwardly" or "outward travel," and the distance a wing extends from the scrotum vertically upwardly when the user is seated will be referred to as "upwardly" or "upward travel."

As will be appreciated by one skilled in the art, the device of the embodiments illustrated in a preferred version in FIG. 2 can be provided in a number of sizes and configurations. For example, the first wing (11) and second wing (13) may have increased upward travel to allow for a larger scrotum or for an increased distance of scrotal hang, or for a user with a larger leg. Alternately, the first wing (11) and second wing (13) may have a decreased upward travel to provide less scrotal hang, or to accommodate a user with a smaller leg. Similarly, the first wing (11) and second wing (13) may have various lengths of outward travel to accommodate different sizes of user, and particularly differing thigh sizes. The first wing (11) may be configured with the same upward and outward travel as the second wing (13), or each wing may be individually configured. In the illustrative preferred embodiment, as depicted in FIG. 2, each wing is configured with an overall radius to accommodate the top of a user's thigh, to enhance comfort, retention, and stability of the device in use. As will be appreciated by one skilled in the art, the upward travel and outward travel of each wing work cooperatively with the support member (9) to determine the fit of the device and the location of the support member (9) with respect to the user's scrotum.

In the depicted preferred embodiment of FIG. 2, the support member (9) is a cup with a mouth wider than the user's scrotum and the wings are radiused and integral to the cup. One or more wings may alternatively be detachably attached to the support member (9) within the scope and spirit of this invention. Further, as device within the scope and spirit of this invention may include three, four, or more wings. As will be appreciated by one skilled in the art, a number of attachment locations and configurations of wings, and of attachment of wings to support member (9) are possible within the scope and spirit of this invention.

The foregoing description and examples have been set forth merely to illustrate the inventions and are not intended to be limiting. Since modifications of the disclosed embodiments incorporating the spirit and substance of the inventions may occur to persons skilled in the art, the invention should be construed broadly to include all variations falling within the scope of the claims and equivalents thereof.

What is claimed is:

1. A male genitalia support device comprising: a disposable cup adapted to prevent a scrotum of a user from undue hang, the disposable cup comprising a configuration with a profiled cut-out to allow at least a portion of the penis to escape and not be captured by the disposable cup, and at least two disposable adhesive attachment members configured to be detachably attached to at least one of a pair of legs of the user, wherein the at least two disposable adhesive attachment members comprise a first attachment member comprising a first portion and a second portion remote from the first portion, wherein the first attachment member first portion is detachably attached to a first side of the cup and the first attachment member second portion is configured to be detachably attached adhesively to one of the pair of legs of the user; and a second attachment member comprising a first portion and a second portion remote from the first portion, wherein the second attachment member first portion is detachably attached to a second side of the cup opposite the first side of the cup, and the second attachment member second portion is configured to be detachably attached adhesively to the other one of the pair of legs of the user.

2. The device of claim 1, wherein the disposable cup comprises a flexible plastic.

3. The device of claim 2, wherein the flexible plastic of the disposable cup comprises a cellophane.

4. The device of claim 1, wherein at least one of the first adhesive attachment member and the second adhesive attachment member comprises an adhesive ribbon.

5. The device of claim 4, wherein the adhesive ribbon comprises surgical tape.

6. A male genitalia support device for preventing a scrotum of a user from undue hang, comprising;
a rigid cup complementary to a shape of the male scrota, the rigid cup comprising at least two distinct cleanable rigid wings configured to be positioned across a front of one or more thighs of the user for resting thereon; the rigid cup further comprising a cleanable material and having a configuration with a profiled cut-out configured to allow at least a portion of a penis of the user to escape and not be captured by the rigid cup.

7. The device of claim 6, wherein the at least two distinct cleanable rigid wings comprise a first wing depending outwardly and upwardly from a first side of the cup and a second wing distinct from the first wing, the second wing depending outwardly and upwardly from a second side of the cup opposite the first side, wherein the first wing is configured to rest upon one of a user's thighs and the second wing is configured to rest upon the other of the thighs of the user.

8. The device of claim 7, wherein at least one of the first wing and the second wing are integral to the cup.

9. The device of claim 8, wherein at least one of the first wing and the second wing are radiused.

10. The device of claim 9 wherein the device is composed of a dishwasher-safe material.

11. The device of claim 6, wherein the cleanable material of the rigid cup is selected from a group consisting of High-density polyethylene (HDPE), poly vinyl chloride (PVC), polypropylene, Lexan, stainless steel and Polyether ether ketone (PEEK).

12. The male genitalia cup of claim 6, wherein the cup can be configured in a variety of sizes and shapes.

* * * * *